United States Patent
Miyoshi et al.

(10) Patent No.: US 8,147,404 B2
(45) Date of Patent: Apr. 3, 2012

(54) ENDOSCOPE SHAPE DETECTING APPARATUS

(75) Inventors: Yoshitaka Miyoshi, Hachioji (JP); Chieko Aizawa, Hachioji (JP); Kensuke Miyake, Hachioji (JP); Fumiyuki Onoda, Tama (JP); Minoru Sato, Hino (JP); Hiroshi Niwa, Koganei (JP); Tomohiko Oda, Kawagoe (JP)

(73) Assignee: Olympus Corporation, Tokyo (JP)

( * ) Notice: Subject to any disclaimer, the term of this patent is extended or adjusted under 35 U.S.C. 154(b) by 1262 days.

(21) Appl. No.: 11/799,864

(22) Filed: May 3, 2007

(65) Prior Publication Data

US 2007/0208222 A1      Sep. 6, 2007

Related U.S. Application Data

(63) Continuation of application No. PCT/JP2005/020460, filed on Nov. 8, 2005.

(30) Foreign Application Priority Data

Nov. 10, 2004   (JP) .................................. 2004-326872

(51) Int. Cl.
*A61B 1/00*    (2006.01)
*A61B 1/04*    (2006.01)
(52) U.S. Cl. ........................................ 600/145; 600/177
(58) Field of Classification Search .................... 600/17, 600/118, 145, 146, 147, 151
See application file for complete search history.

(56) References Cited

U.S. PATENT DOCUMENTS

| 5,840,024 A  * | 11/1998 | Taniguchi et al. ............ 600/424 |
| 6,059,718 A    | 5/2000  | Taniguchi et al. |
| 6,432,041 B1 * | 8/2002  | Taniguchi et al. ............ 600/118 |
| 6,589,163 B2 * | 7/2003  | Aizawa et al. ................ 600/118 |
| 2002/0169361 A1 | 11/2002 | Taniguchi et al. |
| 2002/0188174 A1 | 12/2002 | Aizawa et al. |
| 2003/0055317 A1 | 3/2003  | Taniguchi et al. |
| 2006/0173289 A1 * | 8/2006 | Aizawa et al. ................ 600/424 |

FOREIGN PATENT DOCUMENTS

| JP | 08-107875   | 4/1996 |
| JP | 2003-245243 | 9/2003 |
| JP | 2003-290129 | 10/2003 |

OTHER PUBLICATIONS

Supplementary European Search Report dated Aug. 4, 2010.

* cited by examiner

*Primary Examiner* — Philip R Smith
(74) *Attorney, Agent, or Firm* — Scully, Scott, Murphy & Presser, P.C.

(57) ABSTRACT

A driving block includes a plurality of magnetic-field generating elements and a driving signal generating section, and the magnetic field generated by the plurality of magnetic-field generating elements is detected by a plurality of magnetic-field detecting elements. A shape calculating block calculates a shape of an insertion portion of an endoscope based on a frequency component corresponding to a frequency of the driving signal in a detection signal detected by the plurality of magnetic-field detecting elements. Oscillation frequency of the reference clock for deciding the frequency of the driving signal is changeably set by the frequency setting section, and the reference clock with oscillation frequency set by the frequency setting section is supplied to both of the driving block and the shape calculating block.

18 Claims, 7 Drawing Sheets

ENDOSCOPE SHAPE DETECTING APPARATUS

CROSS REFERENCE TO RELATED APPLICATION

This application is a continuation application of PCT/JP2005/020460 filed on Nov. 8, 2005 and claims benefit of Japanese Application No. 2004-326872 filed in Japan on Nov. 10, 2004, the entire contents of which are incorporated herein by this reference.

BACKGROUND OF THE INVENTION

1. Field of the Invention

The present invention relates to an endoscope shape detecting apparatus for detecting and displaying an insertion shape and the like of an endoscope inserted into a body cavity.

2. Description of the Related Art

In recent years, there has been used an endoscope shape detecting apparatus which detects a shape and the like of an endoscope inserted, for example, into a body cavity using a magnetic-field generating element and a magnetic-field detecting element, and displays the detected shape by display means.

For example, Japanese unexamined patent publication No. H08-107875 as a first conventional example discloses an apparatus which detects the shape of the endoscope using magnetic fields, and displays the detected shape of the endoscope.

In the apparatus, a plurality of magnetic-field generating elements disposed at a predetermined interval in an insertion portion of the endoscope which is inserted in a body are driven to generate magnetic fields therearound, and three-dimensional positions of the respective magnetic-field generating elements are detected by magnetic-field detecting elements disposed outside the body. Then, a curve continuously linking the detected three-dimensional positions of the respective magnetic-field generating elements is generated, and a three-dimensional shape image representing a model of the insertion portion is displayed by the display means.

An operator, for example, can have a grasp of the position and the insertion shape and the like of a distal end portion of the insertion portion inserted in a body by observing the shape image. This helps the operator smoothly perform the work of inserting the insertion portion into a target region, for example.

In a case where the magnetic fields are generated to detect the shape as described above, it is desirable to perform the shape detection in an environment with less noise which influences the position detection, in order to accurately perform the position detection and calculate the shape of insertion portion based on the position detection. In particular, a noise source of a driving frequency of alternating current signal for driving the magnetic-field generating elements has a great influence on a calculation result of the position detection.

Therefore, in Japanese unexamined patent publication No. 2003-245243 as a second conventional example, driving frequencies of alternating current signals for driving a plurality of magnetic-field generating elements are selectable, and noise detection means detects frequency components of the noise detected in a driving stop state in which the plurality of magnetic-field generating elements are not driven. In addition, the publication discloses an apparatus having a configuration in which the plurality of magnetic-field generating elements are driven based on the alternating current signals of the driving frequencies with less frequency components of the detected noise, and position detection is accurately performed in the environment with less noise.

SUMMARY OF THE INVENTION

An endoscope shape detecting apparatus according to the present invention includes: a driving block including a plurality of magnetic-field generating elements and driving signal generating section for generating a magnetic field by supplying a driving signal to the plurality of magnetic-field generating elements; a detecting block for detecting the magnetic field generated by the plurality of magnetic-field generating elements using a plurality of magnetic-field detecting elements; a shape calculating block for calculating a shape of an insertion portion by calculating positions of the plurality of magnetic-field generating elements disposed in the insertion portion of an endoscope or the plurality of magnetic-field detecting elements, based on a frequency component corresponding to a frequency of the driving signal in a detection signal detected by the plurality of magnetic-field detecting elements; and a frequency setting section for changeably setting oscillation frequency of a reference clock for deciding the frequency of the driving signal; and the reference clock whose oscillation frequency is set by the frequency setting section is supplied both to the driving block and the shape calculating block.

DETAILED DESCRIPTION OF THE PREFERRED EMBODIMENTS

Hereinafter, embodiments are described with reference to the drawings.
(First Embodiment)

Description will be made on the first embodiment of the present invention with reference to FIGS. 1 to 5.

Figure 1:
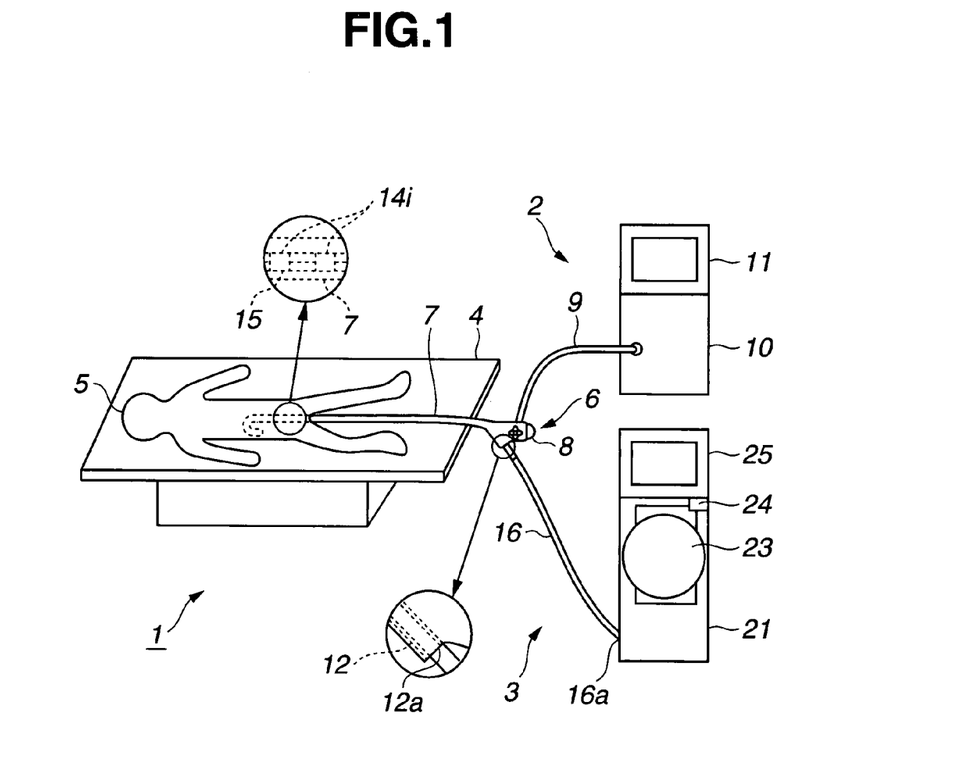
FIG. 1 is a schematic view showing a configuration of an endoscope system according to a first embodiment of the present invention.

As shown in FIG. 1, an endoscope system 1 includes an endoscope apparatus 2 for performing endoscopy, and an endoscope shape detecting apparatus 3 used for assisting the endoscopy according to the first embodiment. The endoscope shape detecting apparatus 3 is used as insertion assisting means when performing an endoscopy by inserting an insertion portion 7 of an electronic endoscope 6 into a body cavity of a patient 5 lying on a bed 4.

The electronic endoscope 6 has an operation portion 8 provided with a bending operation knob, formed at the rear end of the elongated flexible insertion portion 7. A universal cord 9 is extended from the operation portion 8 and connected to a video processor (or a video imaging system) 10.

The electronic endoscope 6 has a light guide inserted therethrough, and transmits illumination light from a light source portion in the video processor 10 to emit the transmitted illumination light through an illumination window formed at the distal end of the insertion portion 7. Thus the affected part or the like is illuminated. An image of the illuminated subject such as the diseased part is formed on an image pickup device located on the image forming position of an objective lens mounted in an observation window adjoining the illumination window. The image pickup device performs photoelectric conversion.

A photoelectrically-converted signal is processed by a video signal processing section in the video processor 10, whereby a standard video signal is generated. Then, an image corresponding to the video signal is displayed on an image observation monitor 11 connected to the video processor 10.

The electronic endoscope 6 includes a forceps channel 12. A probe 15 which includes a plurality of source coils 14a, 14b, . . . , and 14p (hereinafter, generically shown by the reference numeral 14i) serving as magnetic-field generating elements is inserted through an insertion port 12a of the forceps channel 12. Consequently, the source coils 14i are disposed in the insertion portion 7.

A source cable 16, which is extended from the rear end of the probe 15, has a connector 16a provided at the rear end thereof detachably attached to a detecting apparatus 21 as an apparatus main body of the endoscope shape detecting apparatus 3. From the detecting apparatus 21 side, a driving signal is applied to the source coils 14i via the source cable 16 serving as a high-frequency driving signal transmitting section (high-frequency driving signal transmitting means). Consequently, the source coils 14i radiate to the surrounding area electromagnetic waves accompanied by magnetic fields.

In addition, the detecting apparatus 21, which is arranged in the vicinity of the bed 4 on which the patient 5 lies down, has a (sense) coil unit 23 movably provided in up and down directions (freely raised or lowered), and a plurality of sense coils as the magnetic-field detecting elements are arranged in the coil unit 23.

Figure 2:
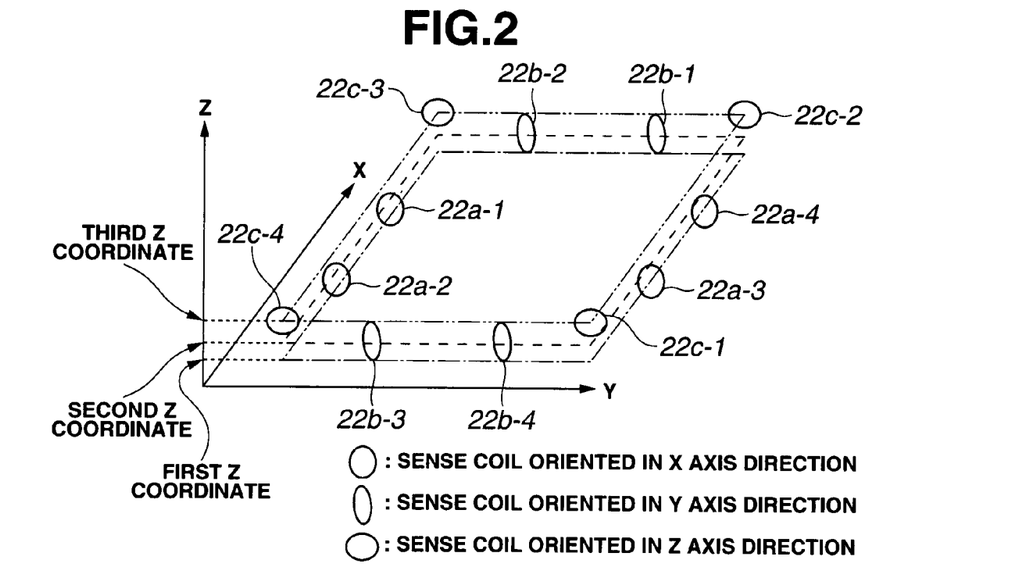
FIG. 2 is a view showing an example of layout of sense coils incorporated in a coil unit using a standard system of coordinates.

More particularly, as shown in FIG. 2, twelve sense coils are arranged in such a manner that: sense coils 22a-1, 22a-2, 22a-3, and 22a-4 are oriented in the direction of, for example, an X axis and the Z coordinates of the centers of the coils are located on, for example, a first Z coordinate; sense coils 22b-1, 22b-2, 22b-3, and 22b-4 are oriented in the direction of a Y axis and the Z coordinates of the centers of the coils are located on a second Z coordinate different from the first Z coordinate; and sense coils 22c-1, 22c-2, 22c-3, and 22c-4 are oriented in the direction of a Z axis and the Z coordinates of the centers of the coils are located on a third Z coordinate different from the first and the second Z coordinates (hereinafter, for simplification, renaming 22a-1, 22a-2, . . . , 22c-14 as 22a, 22b, . . . , 22l and generically showing these by the reference numeral 22j (j=a to l)).

The sense coils 22j are connected to the detecting apparatus 21 via a cable not shown extended from the coil unit 23. The detecting apparatus 21 has an operation panel 24 for enabling a user to operate the apparatus. In addition, the detecting apparatus 21 has a liquid crystal monitor 25 arranged at an upper part thereof as display means for displaying the detected endoscope shape.

Figure 3:
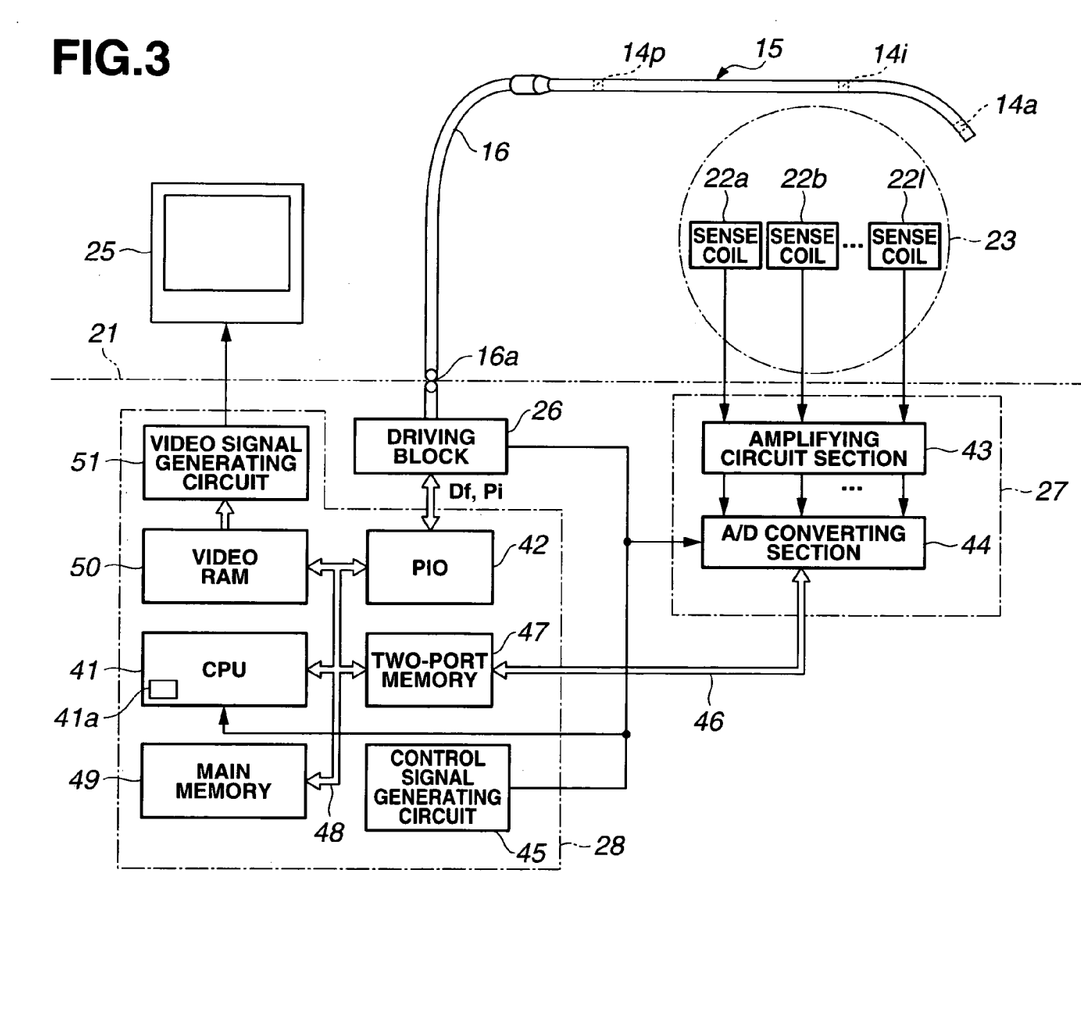
FIG. 3 is a block diagram showing a configuration of an endoscope shape detecting apparatus according to the first embodiment of FIG. 1.

As shown in FIG. 3, the endoscope shape detecting apparatus 3 includes a driving block 26 for driving the source coils 14i in the probe 15, a detecting block 27 for detecting the signals received by the sense coils 22j in the coil unit 23, and a host processor (shape calculating block) 28 for performing signal processing such as shape calculation based on the signals detected in the detecting block 27.

Figure 4:
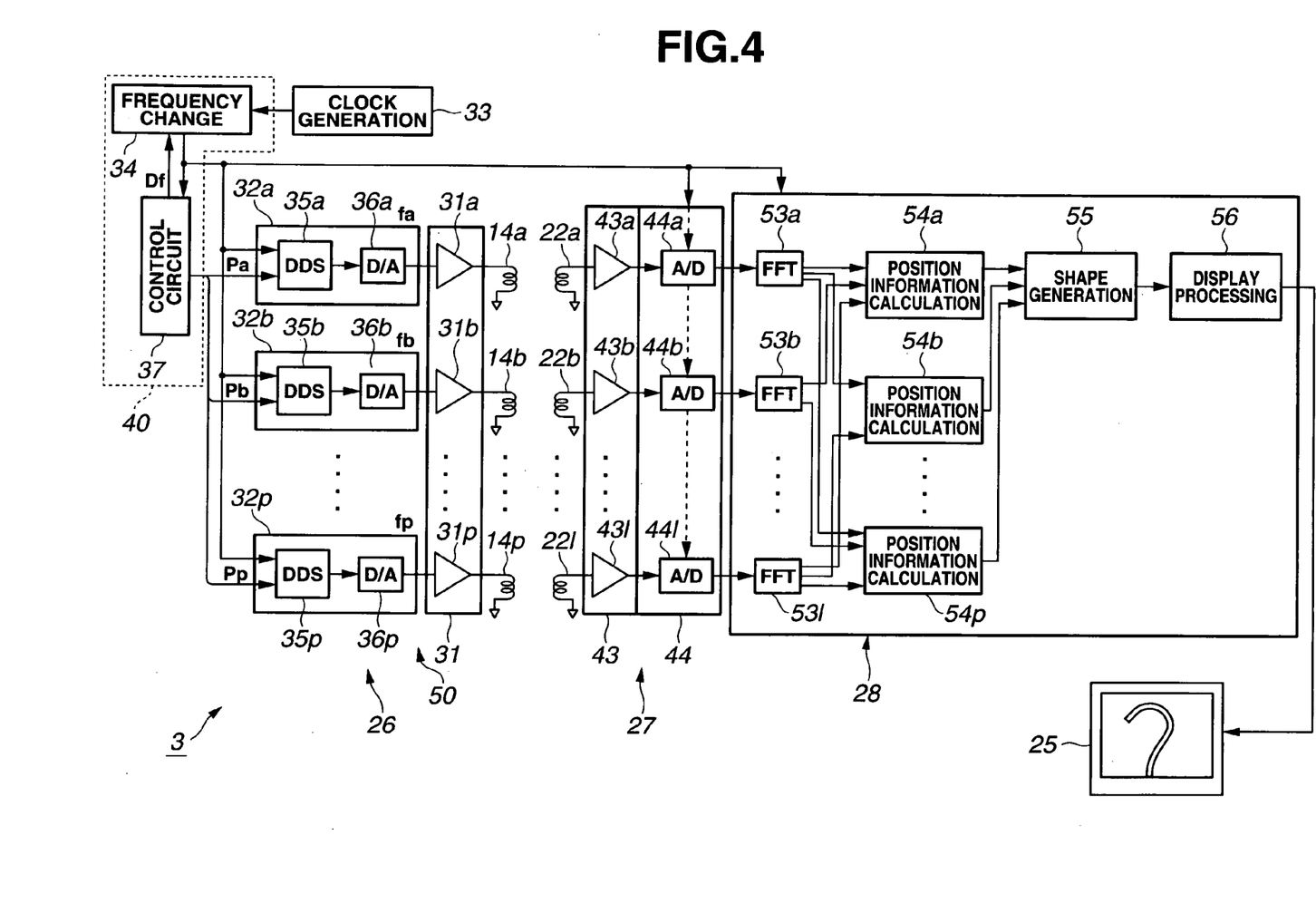
FIG. 4 is a block diagram showing more detailed configurations of a reception block and a control block of FIG. 3.

The probe 15 shown in FIG. 3, which is provided to the insertion portion 7 of the electronic endoscope 6, as mentioned above, has a plurality of, for example, sixteen source coils 14i for generating magnetic fields disposed at a predetermined interval. The source coils 14i are respectively driven by coil driving circuits 31i configuring the driving block 26, as shown in FIG. 4. Note that the sixteen coil driving circuits 31i are shown as a coil driving circuit section 31.

As shown in FIG. 4, the coil driving circuit section 31 has sixteen oscillators 32i (i=a to p) so that the sixteen source coils 14i can be driven by sine-wave driving signals of different frequencies, respectively. The coil driving circuit section 31 amplifies the sine waves from the oscillators 32i by the coil driving circuits 31i to generate the driving signals, thereby driving the source coils 14i. That is, the oscillators 32i and the coil driving circuits 31i configure a driving signal generating circuit for driving the source coils 14i. In other words, the oscillators 32a to 32p and the coil driving circuits 31a to 31p configure a driving signal generating section 50.

Furthermore, in the present embodiment, there is provided a clock generator 33 for generating a clock. The clock generated by the clock generator 33 is outputted as a reference clock whose frequency is changed to be set by a frequency changing circuit 34 configuring the frequency setting section 40.

Then, the reference clock whose frequency is changed to be set via the frequency changing circuit 34 is supplied in common to each of the oscillators 32i, and the respective oscillators 32i output sine waves of different frequencies fi (specifically, from fa to fp) to the coil driving circuits 31i based on the common reference clock supplied thereto. Each of the oscillators 32i includes a direct digital synthesizer (abbreviated as DDS) 35i for outputting a sine wave in digital waveform having a single frequency component in accordance with a digital parameter value set in advance based on the reference clock to be supplied, and a D/A converter 36i for D/A converting the output of the DDS 35i.

The respective DDSs 35i have input ends to which the above-described common reference clock is supplied, and input ends for the parameter to decide oscillation frequency, to which different parameter values Pi set in advance via the control circuit 37 is inputted, respectively. Then the respective DDSs 35i generate digital sine waves of frequencies each corresponding to the set parameter values Pi, and convert the digital sine waves to analog sine waves via the D/A converter 36i to output the converted sine waves as driving signals to the coil driving circuits 31i. In the frequency changing circuit 34, the frequency changing operation is controlled, via the control circuit 37, for example, under the control of (a CPU 41 configuring the) host processor 28. That is, as shown in FIG. 4, the frequency setting section 40 includes the control circuit 37 and the frequency changing circuit 34. For example, in the frequency changing circuit 34, frequency setting data Df stored in a memory and the like incorporated therein is changed to be set, via the control circuit 37, in response to the control signal from the host processor 28. Then, the frequency changing circuit 34 outputs the reference clock to be used in common, whose frequency corresponds to the set frequency setting data Df.

The reference clock outputted from the frequency changing circuit 34 is supplied to (the DDSs 35$i$ of) the driving block 26, as described above. Furthermore, the reference clock is also supplied to respective A/D converters 44$j$ in the detecting block 27, FFT sections (FFT means) 53$j$ for separating and extracting the signals of the frequency components corresponding to the driving frequencies or position information calculation sections (position information calculation means) 54$j$ in order to calculate position information, in the host processor 28 of FIG. 4, and the CPU 41 (performs separating and extracting processings of frequency components using software) in FIG. 3. Note that, the host processor 28 including the CPU 41 and the like shown in FIG. 3 is shown as a function configured by the software such as the FFT sections 53$j$ in a host processor section 28 in FIG. 4.

Thus, the present embodiment has a configuration in which the reference clock outputted from the frequency changing circuit 34 is supplied in common to the driving block 26, the detecting block 27, and the host processor 28 for performing shape calculation.

In addition, also in a case where the frequencies of driving signals for actually driving the respective source coils 14$i$ are changed in accordance with the change setting of the common reference clock, the extraction of signal components of the same frequency corresponding to the change can be easily performed also by the host processor 28 side in synchronization with the driving block 26 side. Furthermore, also in a case of calculating phases of the extracted frequency components which are used for calculating the distance between the frequency components, the phases can be accurately detected with a simple configuration, since the common reference clock is used on both of the driving side and the detecting side. Therefore, accurate calculation of distance is possible.

The frequency setting data Df stored in the frequency changing circuit 34 is sent to the control circuit 37 in the driving block 26 shown in FIG. 4 by the CPU (Central Processing Unit) 41 for performing a calculation processing of the endoscope shape, and the like, in the host processor 28 in FIG. 3, via a PIO (Parallel Input-Output circuit) 42. Then, the frequency setting data Df is changed by the control circuit 37. After that, the reference clock whose oscillation frequency corresponds to the frequency setting data Df is outputted from the frequency changing circuit 34.

Thus, only by changing the frequency of the common reference clock based on the change of the frequency setting data Df, the frequencies fi of the respective oscillators 32$i$ can be changed according to the parameter values Pi set in advance, respectively.

On the other hand, the twelve sense coils 22$j$ in the coil unit 23 (shown by 22$a$ to 22$l$ in FIGS. 3 and 4 by simplifying the way of notation in FIG. 2, as described above) are connected to a sense coil signal amplifying circuit section (simply abbreviated as an amplifying circuit section) 43 configuring the detecting block 27.

The amplifying circuit section 43 includes twelve amplifying circuits 43$j$ respectively connected to the sense coils 22$j$ (j represents a to l) as shown in FIG. 4.

The detection signals detected by the sense coils 22$j$ are, after being amplified by the amplifying circuits 43$j$, inputted to the A/D converters 44$j$ configuring an A/D converting section 44 to be A/D converted into digital detection signals.

Note that the reference clock outputted from the frequency changing circuit 34 is supplied to (the respective A/D converters 44$j$ in) the A/D converting section 44, whereby the A/D conversion is performed in synchronization with the reference clock.

Output data from the A/D converting section 44 is inputted to the host processor 28. The host processor 28 has the configuration shown in FIG. 3 and the functional configuration thereof is shown in FIG. 4.

As shown in FIG. 3, the reference clock outputted from (the frequency changing circuit 34 in) the driving block 26 is supplied to a control signal generating circuit 45 in the host processor 28, and the control signal generating circuit 45 generates a control signal of timing synchronized with the reference clock.

Then, the output data outputted from the A/D converting section 44 is written into a two-port memory 47 via a local data bus 46, in response to the control signal synchronized with the reference clock, which is generated by the control signal generating circuit 45.

Furthermore, the CPU 41 reads out, via an internal bus 48, the digital data written into the two-port memory 47 in response to the control signal generated by the control signal generating circuit 45, uses a main memory 49, and performs a frequency analysis processing (Fast Fourier Transform: FFT) on the digital data, as described later.

Then, the CPU 41 separates and extracts magnetic field detection information of the frequency components coincident with the driving frequencies of the respective source coils 14$i$, and calculates spatial position coordinates of the respective source coils 14$i$ provided in the insertion portion 7 of the electronic endoscope 6, based on the respective digital data of the extracted magnetic field detection information.

In the present embodiment, the data of the parameter values Pi set in the DDSs 35$i$ of the respective oscillators 32$i$ are stored, for example, in a memory (or a register) 41$a$ incorporated in the CPU 41 of FIG. 3.

Then, the CPU 41 calculates the frequencies fi of the respective oscillators 32$i$ by reading out the frequency setting data Df stored in the frequency changing circuit 34, and the parameter values Pi from the memory 41$a$, to separate and extract the magnetic field detection information of the frequency components corresponding to the driving frequencies at which the respective source coils 14$i$ are driven.

In addition, the CPU 41 estimates an insertion state of the insertion portion 7 of the electronic endoscope 6 from the calculated position coordinate data, to generate display data forming an endoscope shape image and output the data to a video RAM 50. The display data written into the video RAM 50 is read out by a video signal generating circuit 51 and converted into an analog video signal to be outputted on the liquid crystal monitor 25. The liquid crystal monitor 25 which receives the analog video signals inputted thereto displays on the display screen an image of insertion shape of insertion portion 7 of the electronic endoscope 6.

The CPU 41 calculates the magnetic field detection information corresponding to the respective source coils 14$i$, that is, information on electromotive force generated in the respective sense coils 22$j$ (amplitude values of the sine-wave signals) and phase. Note that the phase information includes the polarity (plus and minus) of the electromotive force.

As shown in FIG. 4, when describing the functional configuration of the host processor 28, the digital detection data outputted from the A/D converting section 44 is inputted to FFT sections 53$j$ realized by dedicated circuits and programs, and the FFT sections 53$j$ perform a frequency analysis processing at high speeds on the detection data. Then, the FFT sections 53$j$, on the basis of the analysis processing result, extract the magnetic field detection information of the frequency components coincident with the driving frequencies of the respective source coils 14i to output the extracted information.

That is, the frequency analysis data by the respective FFT sections 53j are separated by each driving frequency component to be inputted to position information calculation sections 54a to 54p realized by the dedicated circuits and programs. The respective position information calculation sections 54i (i represents one of 54a to 54p) perform a processing for calculating the spatial position coordinates (position information) of the respective source coils 14i from the amplitude values and phase values in the detection data using the positions of the respective sense coils 22j as references.

The position information calculated by each of the position information calculation sections 54i is inputted to a shape generating section (shape generating means) 55 realized by a dedicated circuit and a program. The shape generating section 55 performs an interpolation processing and the like based on the position information of the respective source coils 14i to generate the shape of the insertion portion 7 and outputs the shape to a display processing circuit 56.

The display processing circuit 56 outputs on the liquid crystal monitor 25 serving as insertion shape display means a video signal of the calculated insertion shape of the insertion portion 7 such that the insertion shape (endoscope shape) of the insertion portion 7 is displayed on the display screen of the liquid crystal monitor 25.

In the present embodiment, as described above, the common reference clock is supplied not only to the respective oscillators 32i in the driving block 26 but also to the host processor 28. Furthermore, changing the frequency of the reference clock enables the frequencies fi of all the oscillators 32i to be uniquely changed according to the set parameter values Pi. In addition to this, also on the host processor 28 side, by referring to the value of the reference clock and the parameter values Pi, the frequencies to be separated and extracted are automatically calculated, and thereby the position calculation or the like of the source coils 14i can be automatically performed (without requiring the user to set the frequencies to be separated and extracted).

Note that, when measuring environmental noise as described below, the detecting block 27 and the host processor 28 are operated in a state where the respective source coils 14i are not driven so as to make the detecting block and host processor serve also as a noise detecting section for detecting noise.

Figure 5:
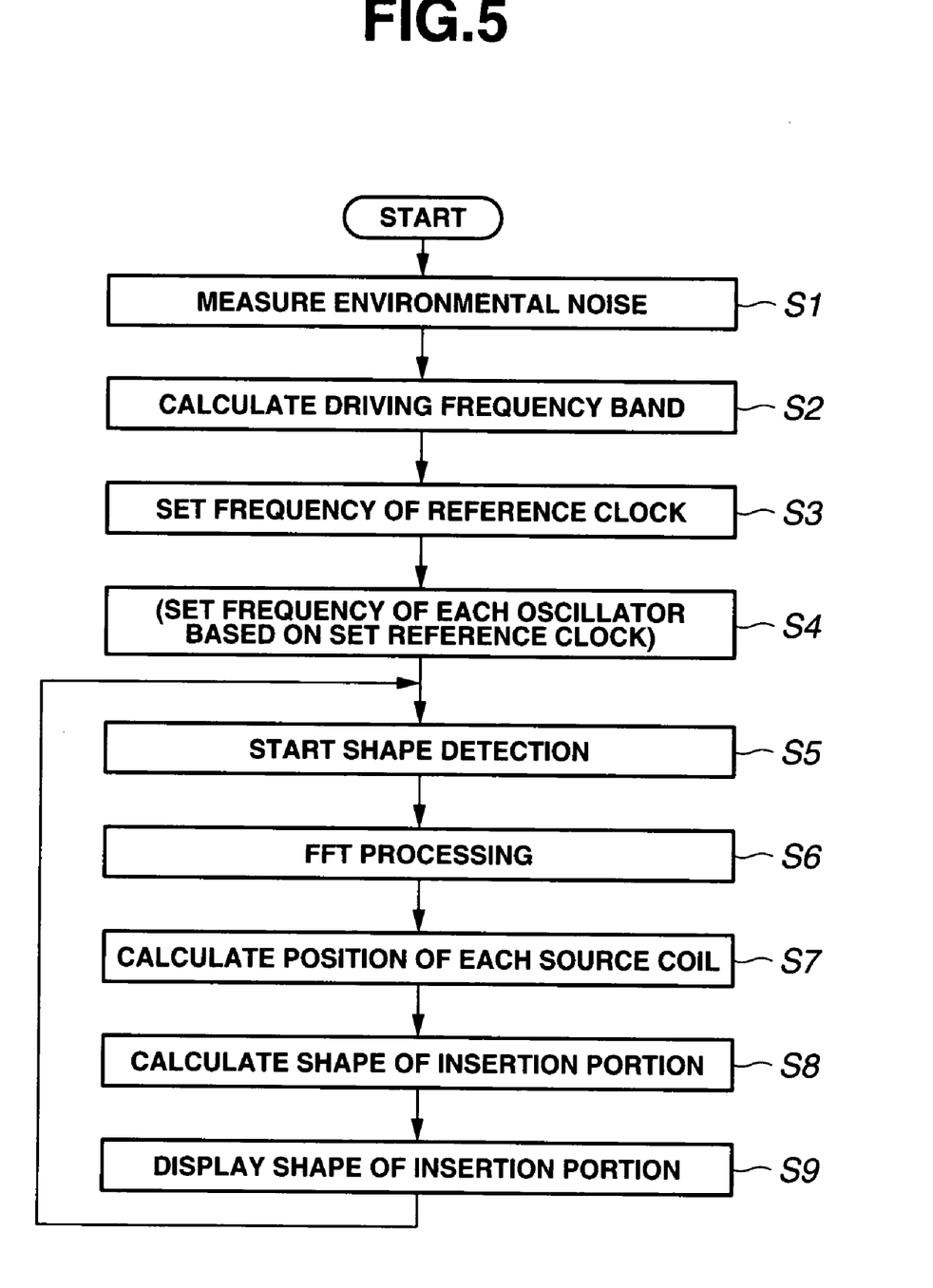
FIG. 5 is a flowchart showing an operation content of the first embodiment.

The operation of the present embodiment will be described with reference to FIG. 5. When the power source of the endoscope shape detecting apparatus 3 is turned on to be set in an operable state, the CPU 41 starts measuring the environmental noise in the first step S1.

In this case, without driving the respective source coils 14i by the driving signals, signal detection is performed by the sense coils 22j similarly as in a case where the source coils 14i are driven. That is, this is equivalent to measuring the noise level, since the detection of signals in the magnetic fields is performed in the absence of signals for generating the magnetic fields.

In this case, the frequency setting data Df stored in the frequency changing circuit 34 are changed, and a plurality of groups of frequencies available for the shape detection are scanned (noise is measured respectively at the plurality of groups of driving frequencies in a state where no driving signal is applied).

Then, based on the measurement result at the plurality of groups of driving frequencies in the step S1, the CPU 41 calculates a driving frequency band used for actually detecting the shape in the next step S2. In this case, the frequency band in which the average noise level is the lowest in the measurement result in the step S1 is, for example, calculated as the driving frequency band.

Furthermore, in the step S3, the CPU 41 sets the frequency setting data Df such that the reference clock corresponding to the frequency band in which the average noise level is the lowest is outputted from the frequency changing circuit 34. As shown in the next step S4, the frequency changing circuit 34 supplies the reference clock to the respective oscillators 32i. According to this, the respective oscillators 32i oscillate at the frequencies fi corresponding to the frequency of the reference clock, according to the parameter values Pi set in advance. The processing in the step S4 is automatically performed as shown by the parenthesis in FIG. 5.

That is, by performing the processings from the steps S1 to S4, completed is the setting of frequency of the reference clock outputted from the frequency changing circuit 34 such that the shape detection is performed at the frequency in which the environmental noise is the lowest, and operation of shape detection starts in the step S5.

In the step S5, when the operation of shape detection starts, the respective source coils 14i are driven by the driving signals with driving frequencies fi, respectively, to generate alternating current magnetic fields therearound. The respective alternating current magnetic fields are amplified by the sense coils 22j to be A/D converted.

Then, as shown in the step S6, the A/D converted output signals of the detecting block 27 are subject to the frequency analysis processing (FFT processing) by the respective FFT sections 53 in the host processor 28.

The frequency analysis data obtained as a result of frequency analysis by the FFT sections 53j with respect to the detection signals of the respective sense coils 22j are separated for each of the frequency components respectively corresponding to the driving frequencies fi of the respective source coils 14i, to be distributed to each of the position information calculation sections 54i. Then, as shown in the step S7, each of the position information calculation sections 54i calculates position data of each of the source coils 14i.

The above-described FFT processing and the processing of separating the frequency analysis data for each of the frequency components respectively corresponding to the driving frequencies fi of each of the source coils 14i are performed by the CPU 41 in FIG. 3. At this time, the CPU 41 easily calculates the driving frequencies fi of each of the source coils 14i based on the parameter values Pi stored in the memory 41a and the frequency value of the reference clock.

Therefore, the present embodiment enables the CPU 41 to separate the frequency components respectively corresponding to the values of the driving frequencies fi of each of the source coils 14i, without a setting operation to the CPU 41 by a user. As a result, an operatability is greatly improved.

The calculated position data of each of the source coils 14i is inputted to the shape generating section 55. As shown in Step S8, the shape generating section 55, for example, interpolates between the positions of the respective source coils 14i to generate shape data of the insertion portion 7 in which the respective source coils 14i are disposed.

The shape data is inputted to the display processing circuit 56. As shown in the step S9, the display processing circuit 56 generates image data displaying the shape of the insertion portion to output the data to the liquid crystal monitor 25 such that the shape of the insertion portion is displayed on the display screen.

The processings from the step S5 to the step S9 are continuously and repeatedly performed at a predetermined interval. Therefore, after the processing of the step S9, the procedure returns to the step S5 and next shape detection is started.

According to the present embodiment configured to perform such operations, when the driving frequency band of the driving signals is set in the frequency band with low noise level, each of the driving frequencies fi is set by changing the setting of the frequency of the common reference clock itself, and the reference clock is supplied in common to the driving block 26 side and the host processor 28 side for performing the shape calculation. As a result, the setting of frequencies necessary for the position calculation and the like is automatically performed without the setting operations for changing frequencies which are required to be performed in each section, thereby enabling accurate shape calculation.

That is, according to the present embodiment, in a more simplified circuit configuration, it is possible to accurately detect and display the endoscope shape with less influence by noises.

(Second Embodiment)

Figure 6:
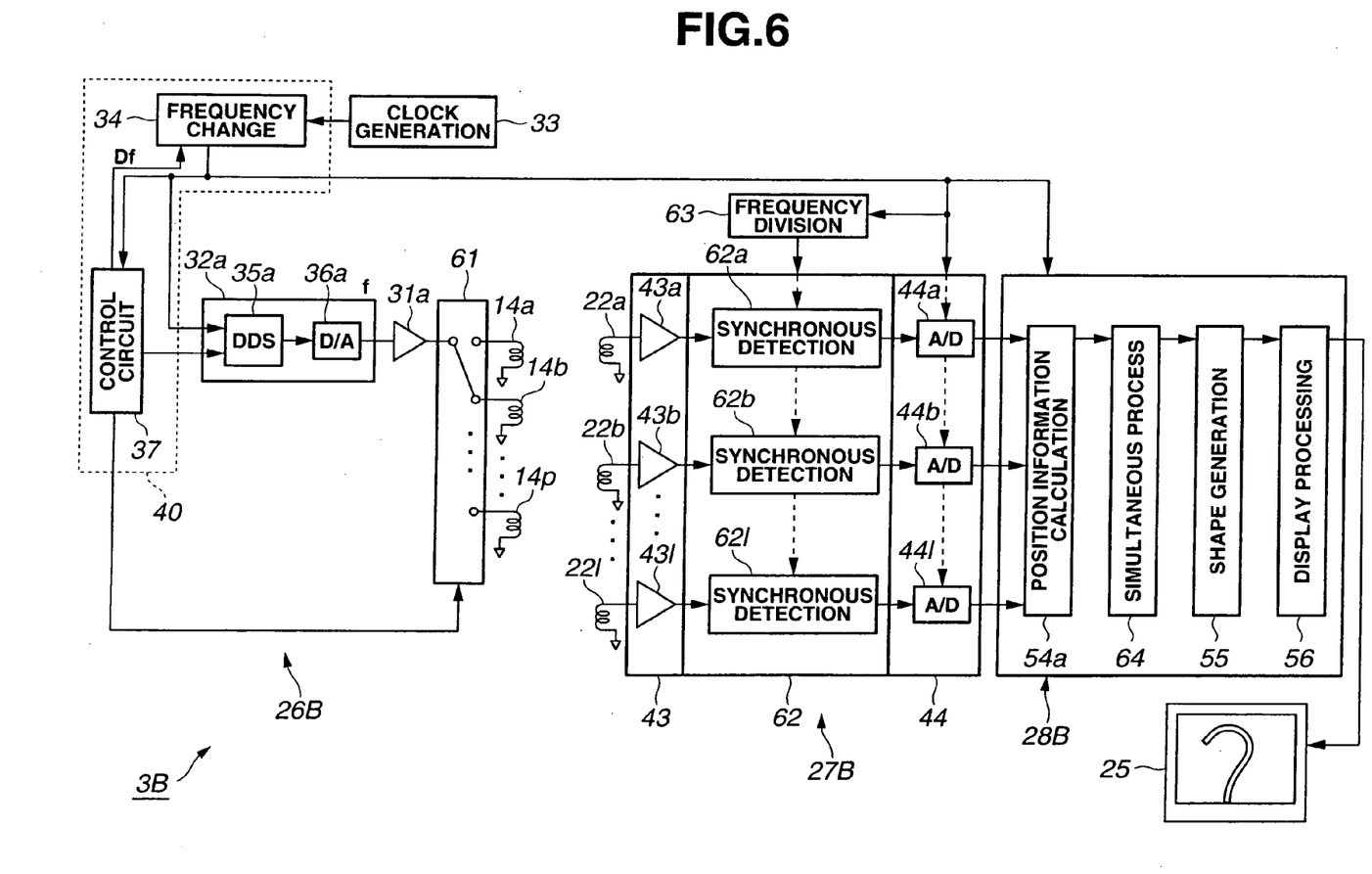
FIG. 6 is a block diagram showing a configuration of the endoscope shape detecting apparatus according to the first embodiment of the present invention.
Figure 7:
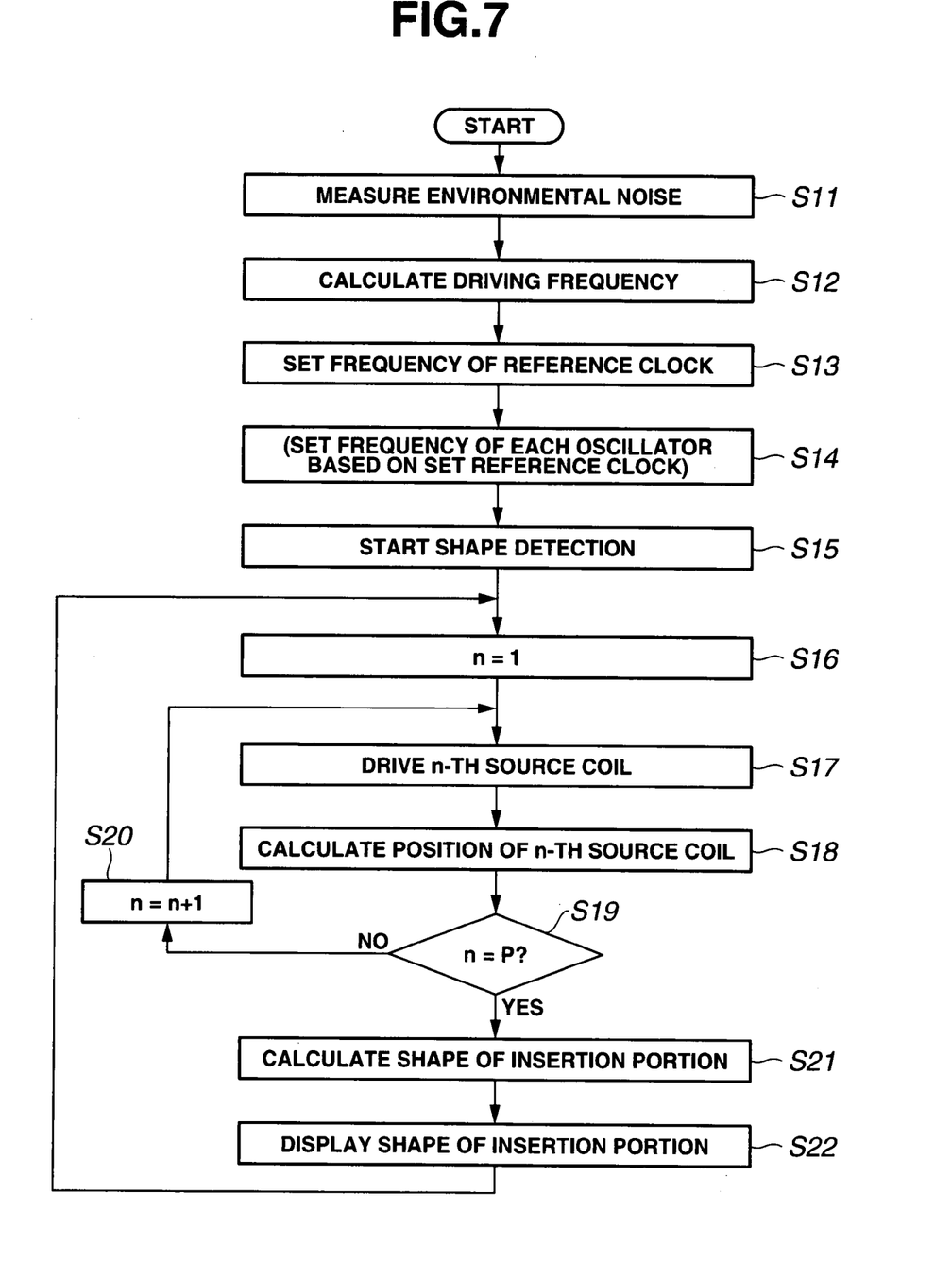
FIG. 7 is a flowchart showing an operation content of a second embodiment.

Next, the second embodiment of the present invention will be described with reference to FIGS. 6 and 7. FIG. 6 shows a configuration of an endoscope shape detecting apparatus 3B of the second embodiment.

The endoscope shape detecting apparatus 3B accurately detects positions of the source coils 14i using synchronous detection.

The endoscope shape detecting apparatus 3B shown in FIG. 6 includes a driving block 26B, a detecting block 27B, a host processor 28B, and a liquid crystal monitor 25.

The driving block 26B of the present embodiment has a configuration in which there is provided only one system of oscillator and coil driving circuit, instead of the plurality of oscillators 32a to 32p and the coil driving circuits 31a to 31p, in the driving block 26 shown in FIG. 4, and output signal of the coil driving circuit 31a is applied, via a multiplexer 61, for example, to sixteen source coils 14i to sequentially drive, that is, drive the source coils 14i in a time-division manner. Note that the multiplexer 61 is sequentially switched over at a predetermined cycle in response to a switch control signal from the control circuit 37.

Furthermore, the detecting block 27B in the present embodiment has a configuration in which synchronous detection circuits 62j are provided between amplifying circuits 43j and A/D converters 44j in the detecting block 27 in FIG. 4. That is, a synchronous detection circuit section 62 configured by twelve synchronous detection circuits 62j, for example, is provided between an amplifying circuit section 43 and an A/D converting section 44.

In the first embodiment, the respective source coils 14i are driven respectively by the driving signals with different driving frequencies fi. Meanwhile, in the present embodiment, the respective source coils 14i are sequentially driven by a driving signal with one driving frequency f, for example. However, also in the present embodiment, noise level is detected as described later, and based on the detection result, the frequency with low noise level is set as the driving frequency f for driving the respective source coils 14i. That is, the driving frequency f is set from among a plurality of frequencies, based on the detection result of the noise level.

In addition, also in the present embodiment, in a case of setting the driving frequency f with low noise level from among the plurality of frequencies, the setting is performed by changing the frequency of the reference clock supplied to the oscillator 32a by the frequency changing circuit 34. In addition, the reference clock outputted from the frequency changing circuit 34 is supplied also to the host processor 28B.

A reference signal of a clock synchronous with the driving frequency f of the driving signal by which the source coils 14i are driven is generated by dividing the frequency of the reference clock, which is outputted via the frequency changing circuit 34, by the frequency division circuit 63. Then the generated reference signal is inputted to each of the synchronous detection circuits 62j. Then, based on the reference signal, after input signals are reversed for every half-period of the reference signal, output signals are obtained through a low-pass filter. As a result, detection signals having the frequency component same as that of the reference signal are extracted, and different frequency components are attenuated.

Thus, the synchronous detection circuits 62j extract the signal components of the same frequency coincident with the driving frequency f of the driving signal from the input signals inputted after being amplified by the amplifying circuits 43j. In addition, the reference signal in this case is generated from the common reference clock, so that the phase of the reference signal completely coincides with that of the driving frequency f of the driving signal (phase difference is zero). Therefore, the detection signals can be obtained with a good S/N ratio. In addition, in reality, phase differences according to the distances between the source coils 14i and the sense coils 22j are generated, and position information is obtained based on the output levels of the detection signals corresponding to the phase differences.

The respective signals synchronously detected by the respective synchronous detection circuits 62j are converted into digital data by the A/D converters 44j, and thereafter inputted to the host processor 28B.

The host processor 28B includes a position information calculation section (position information calculation means) 54a for calculating position information of the driven source coils 14i, a simultaneous processing circuit 64 for storing, in a memory and the like, position information of each of the sixteen source coils sequentially calculated by the position information calculation section 54a and for generating simultaneously processed position information, a shape generating section 55 for performing shape generation processing based on the simultaneously processed position information, and a display processing circuit 56.

In FIG. 4, the sixteen position information calculation sections 54a to 54p are provided. However, the present embodiment has the configuration in which one position information calculation section 54a performs a time-division processing.

The operation of the present embodiment will be described with reference to FIG. 7. Also in the present embodiment, when the power source of the endoscope shape detecting apparatus 3B is turned on and the operation of the endoscope shape detecting apparatus 3B starts, the CPU 41 having a function as control means in the host processor 28 starts measuring environmental noise in the first step S11 similarly as in the case in FIG. 5.

In this case, the source coils 14i are not driven, and the noise level is measured by detecting signals using the sense coils 22j in a no-signal state in which the source coils 14i are not driven. At this time, the frequency setting data Df stored in the frequency changing circuit 34 is changed and a plurality of frequencies available for the shape detection are scanned.

Then, based on the measurement result in the plurality of frequencies in the step S11, the CPU 41 calculates in the next step S12 the driving frequency f to be used actually. In this case, the frequency whose average noise level is the lowest in the measurement result in the step S11, for example, is calculated as the driving frequency f.

In addition, in the step S13, the CPU 41 sets the frequency setting data Df such that the reference clock, the frequency of which corresponding to the driving frequency f whose average noise level is the lowest, is outputted from the frequency changing circuit 34. Then, as shown in the next step S14, the reference clock is supplied to the oscillator 32a, and the oscillator 32a oscillates at the driving frequency f whose noise level is the lowest based on the parameter value set in advance. The processing in the step S14 is automatically performed as shown by the parenthesis in FIG. 7.

In the first embodiment, each driving frequency band is calculated in a case where sixteen different frequencies are used at one time, for example. However, in the present embodiment, only one driving frequency f has to be calculated, so that the frequency whose environmental noise is the lowest is calculated, for example, and the calculated frequency is used as the driving frequency f.

Then, in the next step S15, the shape detection operation is started.

The control circuit 37 sequentially selects the source coils 14i to which driving signal is applied via a multiplexer 61 to drive each of the source coils 14i in a time-division manner. To this end, in the step S16, the parameter n of the source coil number is set to 1. Specifically, the CPU 41 controls the multiplexer 61 to select the source coils via the control circuit 37, and sets the source coil 14i to be turned on as the first source coil 14a.

Then, in the next step S17, the n (=1)-th source coil 14a is driven by the driving signal. The magnetic field generated by the source coil 14a is detected by each of the sense coils 22j, and signal components of the same frequency components are extracted via the synchronous detection circuits 62j to be inputted to the position information calculation section 54a.

Then, as shown in the step S18, the position information calculation section 54a calculates the position of the n (=1)-th source coil 14a based on the data detected by the twelve sense coils 22j and inputted after the synchronous detection. After that, in the next step S19, it is determined whether or not n is equal to (the last number) p (=16). In a case where n is not equal to p, n is set to a value obtained by adding 1 to n in the step S20, and the procedure returns to the step S17 to repeat the processings from the steps S17 to S20.

Meanwhile, in a case where n coincides with p, the position calculation of all the source coils 14a to 14p is completed. Accordingly, the procedure proceeds from the step S19 to the processing in the step S21.

In the step S21, the shape generating section 55 performs a processing of calculating the shape of the insertion portion 7 in which the source coils 14a to 14p are disposed, by using the position information of all. of the source coils 14a to 14p and also interpolating between the source coils, for example.

Then, in the next step S22, the display processing circuit 56 generates the image data of the shape of the insertion portion 7, to display the image of the shape of the insertion portion 7 on the liquid crystal monitor 25.

According to the present embodiment, due to the common use of the reference clock and changing means of the frequency of the reference clock, there is no need to change the value to be set at the DDS in the oscillator (oscillating means) in accordance with the setting of the frequency at which the magnetic fields are generated on the driving side, nor to change the frequency of the reference signal on the host processor (shape calculating block) side, for example. Therefore, accurate shape detection and shape display can be easily performed without any labor.

In addition, only one oscillator is used, thereby simplifying the configuration of the driving block side.

(Third Embodiment)

Figure 8:
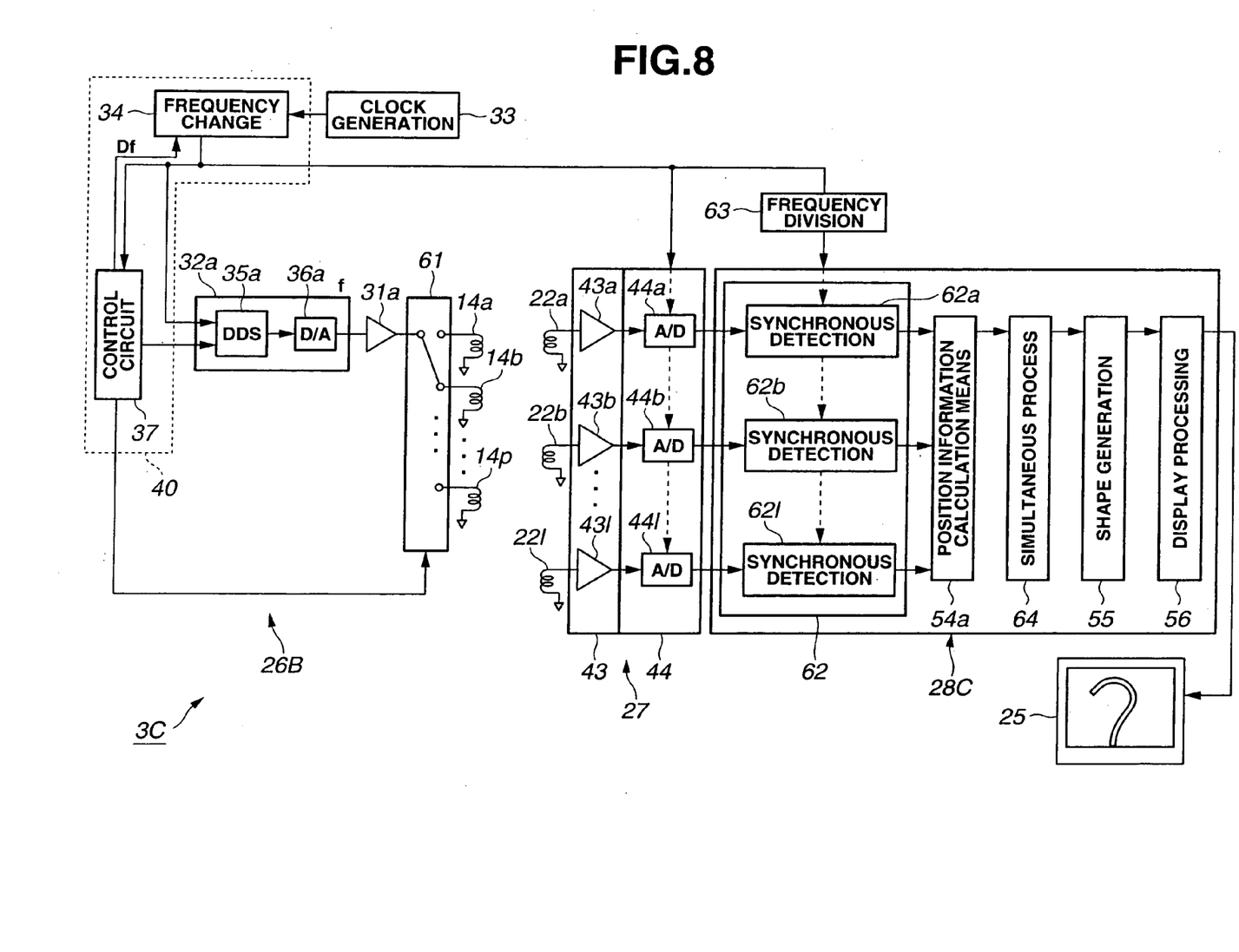
FIG. 8 is a block diagram showing a configuration of an endoscope shape detecting apparatus as a modification example.

Next, the third embodiment of the present invention will be described with reference to FIG. 8. FIG. 8 shows configurations of a driving block 26B, a detecting block 27, and a host processor 28C in an endoscope shape detecting apparatus 3C.

The endoscope shape detecting apparatus 3C accurately detects the positions of the source coils 14i using synchronous detection similarly as in the second embodiment.

In the present embodiment, the function of the synchronous detection circuits 62j of the second embodiment is served by the host processor 28C.

The endoscope shape detecting apparatus 3C shown in FIG. 8 includes the driving block 26B, the detecting block 27, the host processor 28C, and the liquid crystal monitor 25. In the present embodiment, the function of the synchronous detection circuits 62j is served by the software in the host processor 28C.

Other configurations are similar to those in the second embodiment.

The synchronous detection circuits 62j in the present embodiment perform synchronous detection processing by the software in the host processor 28C, as described below.

Digital signal data inputted from the A/D converters 44j is inputted to (the CPU configuring) the synchronous detection circuits 62j. The CPU 41 stores in a register or a memory the signal data inputted in a half-period of the reference signal outputted from the frequency division circuit 63. Meanwhile, as for the signal data inputted in the next half-period, the CPU 41 stores the signal data in the register or the memory after reversing the polarity thereof.

After that, a low-pass filter processing is performed for smoothing these signal data. The signal data subjected to the low-pass filter processing are outputted to the position information calculation section 54a as output data of the synchronous detection circuits 62j.

Other operations are similar to those in the second embodiment. In addition, the effects of the present embodiment are almost similar to those in the second embodiment. That is, due to the common use of the clock and changing means of the frequency of the clock, there is no need to change the value set at the DDS in the oscillator in accordance with the setting of the frequency at which the magnetic fields are generated on the driving side, nor to change the frequency of the reference signal on the host processor (shape calculating block) side, for example. Therefore, accurate shape detection and shape display can be easily performed without any labor.

Furthermore, only one oscillator is used, thereby simplifying the configurations of the driving block side.

Note that, in the first embodiment, it is described that a plurality of source coils 14i are driven respectively by different driving frequencies fi. However, also in the first embodiment, the source coils 14i may be driven in a time-division manner. In this case, the source coils 14i may be driven one by one in a time-division manner same as in the second or the third embodiment. Alternatively, the source coils 14i may be driven in a time-division manner such that a plurality of source coils are driven at a time.

For example, using eight different frequencies as one group of common frequencies, the sixteen sourcecoils may be sequentially (cyclically) driven such that eight source coils are driven at one time by the group of common frequencies.

Note that, in the above description, in order to perform shape detection at the frequency with less influence of noise, the frequency of the reference clock itself is changed and the reference clock is supplied to both sides of the driving signal oscillating section and the shape calculation section.

As a modification example, it may be configured such that a common reference clock whose frequency is not changed is supplied to (the oscillating section of) the driving block and the shape calculation section, and then the parameter value of the DDS 35*i* for deciding the oscillation frequency of the oscillating section in the driving block is changed to change the oscillation frequency of the driving side, and the parameter value is supplied also to (the frequency separating and extracting section of) the shape calculation section, thereby performing accurate position calculation and the like.

Note that, in the above embodiments and the like, description was made on the configuration in which the probe 15 having source coils 14*i* disposed therein is disposed in the forceps channel 12 of the electronic endoscope 6. However, the present invention is not limited to the configuration. It may be configured that the source coils 14*i* are disposed in the insertion portion 7 of the electronic endoscope 6 along the longitudinal direction of the insertion portion. That is, the source coils 14*i* may be incorporated in the insertion portion 7 of the electronic endoscope 6.

Furthermore, in the above embodiments and the like, description was made on the configuration in which the source coils 14*i* for generating magnetic fields are disposed in the insertion portion 7 of the electronic endoscope 6, and the sense coils 22*j* for detecting the magnetic fields are disposed outside a body. However, the present invention is not limited to the configuration, and it may be configured that the sense coils 22*j* are disposed on the insertion portion 7 side and the source coils 14*i* are disposed outside the body.

As described above, the present invention eliminates the trouble of setting such as change of frequency, and enables the accurate position detection and the like.

Note that, the embodiments and the like configured by partially combining each of the above-described embodiments, for example, are also included in the present invention.

The present invention is not limited to the above described embodiments, and various changes and modifications can be made without departing from the spirit of the present invention.

What is claimed is:

1. An endoscope shape detecting apparatus comprising:
a driving block including a plurality of magnetic-field generating elements and driving signal generating section for generating a magnetic field by supplying a driving signal to the plurality of magnetic-field generating elements;
a detecting block for detecting the magnetic field generated by the plurality of magnetic-field generating elements using a plurality of magnetic-field detecting elements;
a shape calculating block for calculating a shape of an insertion portion by calculating positions of the plurality of magnetic-field generating elements disposed in the insertion portion of an endoscope or the plurality of magnetic-field detecting elements, based on a frequency component corresponding to a frequency of the driving signal in a detection signal detected by the plurality of magnetic-field detecting elements;
a frequency setting section for changeably setting oscillation frequency of a reference clock for deciding the frequency of the driving signal, wherein the reference clock whose oscillation frequency is set by the frequency setting section is supplied both to the driving block and the shape calculating block; and
a noise detecting section for detecting a noise level based on the detection signal by the plurality of magnetic-field detecting elements in a state where the driving signal is not applied to each of the plurality of magnetic-field generating elements.

2. The endoscope shape detecting apparatus according to claim 1, wherein the driving signal generating section generates a driving signal whose frequency is decided by a parameter value set in advance, based on input of the reference clock.

3. The endoscope shape detecting apparatus according to claim 2, wherein the shape calculating block is capable of extracting a detection signal with a frequency component coincident with the frequency of the driving signal by referring to the parameter value.

4. The endoscope shape detecting apparatus according to claim 3, wherein the frequency setting section changes the oscillation frequency of the reference clock according to a value of frequency setting data inputted to the frequency setting section.

5. The endoscope shape detecting apparatus according to claim 3, wherein the driving signal generating section simultaneously drives the plurality of magnetic-field generating elements respectively by driving signals with different frequencies.

6. The endoscope shape detecting apparatus according to claim 5, wherein the shape calculating block includes a frequency analyzing section for performing a frequency analysis on the detection signal to separate and extract the detection signal having frequency components coincident with frequencies of driving signals with respectively different frequencies, by using the reference clock and the parameter value.

7. The endoscope shape detecting apparatus according to claim 6, wherein the frequency analyzing section is configured by a Fast Fourier Transform section.

8. The endoscope shape detecting apparatus according to claim 2, wherein the driving signal generating section is configured by a direct digital synthesizer for generating digital signal of sine wave form obtained by frequency-dividing the reference clock, based on the digital parameter value.

9. The endoscope shape detecting apparatus according to claim 1, wherein the noise detecting section detects the noise level based on the detection signal by the plurality of the magnetic-field detecting elements in a state where the oscillation frequency value of the reference clock is changed to be set to various values.

10. The endoscope shape detecting apparatus according to claim 1, wherein the frequency setting section controls to set the oscillation frequency value of the reference clock such that a signal with a frequency whose noise level is low is set as the driving signal, based on a detection result by the noise detecting section.

11. The endoscope shape detecting apparatus according to claim 1, wherein the frequency setting section changes the oscillation frequency of the reference clock according to a value of frequency setting data inputted to the frequency setting section.

12. The endoscope shape detecting apparatus according to claim 1, wherein the noise detecting section detects the noise level based on the detection signal by the plurality of the magnetic-field detecting elements in a state where the oscillation frequency value of the reference clock is changed to be set to various values according to a change of the frequency setting data.

13. The endoscope shape detecting apparatus according to claim 12, wherein the frequency setting section controls to set the oscillation frequency value of the reference clock such that a signal with a frequency whose noise level is low is set as the driving signal, based on a detection result by the noise detecting section.

14. The endoscope shape detecting apparatus according to claim 1, wherein the driving signal generating section simultaneously drives the plurality of magnetic-field generating elements respectively by driving signals with different frequencies.

15. The endoscope shape detecting apparatus according to claim 1, wherein the driving signal generating section drives the plurality of magnetic-field generating elements by driving signals with a common frequency in a time-division manner.

16. The endoscope shape detecting apparatus according to claim 15, wherein the shape calculating block synchronously detects frequency components coincident with the common frequency in the detection signal, based on a reference signal in synchronization with the driving signals with the common frequency, the driving signals driving the plurality of magnetic-field generating elements in a time-division manner.

17. The endoscope shape detecting apparatus according to claim 1, wherein the driving signal generating section drives the plurality of magnetic-field generating elements by a driving signal with one frequency in a time-division manner.

18. The endoscope shape detecting apparatus according to claim 1, wherein the driving signal generating section drives the plurality of magnetic-field generating elements by a driving signal with one frequency in a time-division manner.

* * * * *